(12) United States Patent
Navarro et al.

(10) Patent No.: US 8,269,048 B2
(45) Date of Patent: Sep. 18, 2012

(54) ALLYLIC OXIDATION METHOD FOR THE PREPARATION OF FRAGRANCES USING METAL-ORGANIC COMPOUNDS AND GOLD CATALYSTS

(75) Inventors: Onofre Casanova Navarro, Benicarló (ES); Avelino Corma Canós, Valencia (ES); Sara Iborra Jornet, Valencia (ES)

(73) Assignee: International Flavors & Fragrances Inc., New York, NY (US)

( * ) Notice: Subject to any disclaimer, the term of this patent is extended or adjusted under 35 U.S.C. 154(b) by 217 days.

(21) Appl. No.: 12/888,688

(22) Filed: Sep. 23, 2010

(65) Prior Publication Data
US 2011/0071320 A1 Mar. 24, 2011

(30) Foreign Application Priority Data
Sep. 23, 2009 (EP) .................................... 09382178

(51) Int. Cl.
*C07C 45/28* (2006.01)

(52) U.S. Cl. ........................................ 568/374; 568/819
(58) Field of Classification Search .................. 568/374, 568/819
See application file for complete search history.

(56) References Cited

U.S. PATENT DOCUMENTS

| 4,322,435 | A | * | 3/1982 | Kojima et al. | ................ 514/530 |
| 4,554,363 | A | * | 11/1985 | Vorbrueggen | ................ 549/415 |
| 4,689,345 | A | * | 8/1987 | Kasha et al. | ................... 514/546 |
| 4,855,322 | A | * | 8/1989 | Kasha et al. | ................... 514/546 |

\* cited by examiner

*Primary Examiner* — Sikarl Witherspoon
(74) *Attorney, Agent, or Firm* — Elizabeth M. Quirk; XuFan Tseng; Joseph F. Leightner

(57) ABSTRACT

The present invention refers to a method for allylic catalytic oxidation to obtain $\alpha,\beta$-unsaturated ketones and alcohols from bicyclic compounds reacted with oxygen and catalysts comprising metal-organic compounds and gold nanoparticles. The present invention also relates to a method for the preparation of fragrances using the above methods or products of the above method.

26 Claims, No Drawings

ALLYLIC OXIDATION METHOD FOR THE PREPARATION OF FRAGRANCES USING METAL-ORGANIC COMPOUNDS AND GOLD CATALYSTS

CROSS-REFERENCE to RELATED APPLICATIONS

This application claims priority from European Patent Application No: 09382178.3, Filed 23 Sep. 2009, the contents hereby incorporated by reference as if set forth in its entirety.

1. BACKGROUND OF THE INVENTION

The manufacture of $\alpha,\beta$-unsaturated ketones and alcohols from bicyclic compounds is described in GB Patent No 1,300,970. The process described therein consists of the reaction between a tetra-substituted unsaturated bicyclic compound with a hexavalent chromium compound (e.g. $Na_2Cr_2O_7$) in the presence of short-chain-alkanoic acids as acidic vehicles (e.g. acetic acid), which results in a carbonyl (e.g. ketone) or carbinol (e.g. alcohol) containing product. Another method for manufacturing $\alpha,\beta$-unsaturated ketones and alcohols from bicyclic compounds is described in DE U.S. Pat. No. 2,220,820. In that method, cobalt and/or copper salts (e.g. cobalt (II) naphthenate and copper (II) acetate) are claimed as catalysts.

A particular application of the above conventional methods results in unsatisfactory activity and selectivity as considerable amounts of undesirable alcohols are produced along with the desirable ketone, namely 1,2,3,5,6,7-hexahydro-1,1,2,3,3-pentamethyl-4H-inden-4-one (c.a. 60 weight % conversion and <30 weight % yield to ketone). These substances have strong, persistent, musk woody odours with various rich amber, precious woody, or fine woody overtones. Therefore, the manufacture of said indenones provides novel perfume and fragrance compositions.

The object of the present invention is to provide a method for allylic catalytic oxidations to obtain $\alpha,\beta$-unsaturated ketones and alcohols from bicyclic compounds with oxygen and catalysts comprising metal-organic compounds and a solid catalyst based on gold that favours conversion and selectivity.

2. SUMMARY OF THE INVENTION

The present invention is embodied in the area of the synthesis of chemicals (e.g. fragrances) by means of the usage of homogeneously and heterogeneously catalyzed processes, as an alternative to non-catalyzed processes.

The present invention relates to a method of allylic oxidation, characterized in that a bicyclic compound reactant with the following general Structure I:

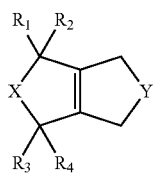

wherein $R_1$, $R_2$, $R_3$ and $R_4$ stand for alkyl groups, X stands for —$CHR_5$— or —$CHR_5$—$CHR_6$—, Y stands for —$CHR_7$— or —$CHR_7$—$CHR_8$— and $R_5$, $R_6$, $R_7$ and $R_8$ stand for hydrogen or alkyl groups, is oxidized with an oxygen-containing gas in presence of a metal-organic compound and a supported gold catalyst, in order to obtain an $\alpha,\beta$-unsaturated ketone and/or alcohol, wherein a carbonyl and/or a carbinol group is in the Y-containing ring.

The present invention refers to a method for the preparation of fragrances comprising an allylic catalytic oxidation as described in the preceding paragraph to obtain $\alpha,\beta$-unsaturated ketones and alcohols.

The present invention refers to a method for the preparation of fragrances comprising an allylic catalytic oxidation to obtain $\alpha,\beta$-unsaturated ketones and alcohols from bicyclic compounds with oxygen and catalysts comprising metal-organic compounds and gold nanoparticles.

The reactants include bicyclic compounds which contain at least one unsaturation and in such a configuration that at least one allylic position occurs. The reactants also include oxygen or an oxygen-containing gas. The products obtained by this improved process are alcohols, ketones, or mixtures thereof that correspond to the said reactants, in particular said bicyclic reactants, in such a configuration that carbonyl, carbinol groups, or mixtures thereof, are located in the allylic position.

The catalysts used to carry out this reaction consist of metal-organic compounds, such as homogeneous metal-organic compounds, and supported gold.

3. DETAILED DESCRIPTION OF THE INVENTION

The present invention is hereinafter detailed. In the present invention, corresponding $\alpha,\beta$-unsaturated ketones and alcohols are prepared by means of allylic oxidation of bicyclic compounds as raw material with oxygen in the presence of several catalysts.

The present invention relates to a method of allylic oxidation, characterized in that a bicyclic compound reactant with the following general Structure I:

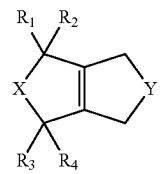

wherein $R_1$, $R_2$, $R_3$ and $R_4$ stand for alkyl groups, X stands for —$CHR_5$— or —$CHR_5$—$CHR_6$—, Y stands for —$CHR_7$— or —$CHR_7$—$CHR_8$— and $R_5$, $R_6$, $R_7$ and $R_8$ stand for hydrogen or alkyl groups, is oxidized with an oxygen-containing gas in presence of a metal-organic compound and a supported gold catalyst, in order to obtain an $\alpha,\beta$-unsaturated ketone and/or alcohol, wherein a carbonyl and/or a carbinol group is in the Y-containing ring.

In the method of the present invention, the allylic oxidation of bicyclic compounds consists of the reaction between a tetra-substituted unsaturated bicyclic compound with oxygen, which results in $\alpha,\beta$-unsaturated ketones and alcohols. Preferably, the tetra-substituted unsaturated bicyclic compounds used as reactant in the present invention have the following Structure I:

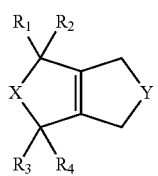

Structure I and the products obtained have the following Structures II and III:

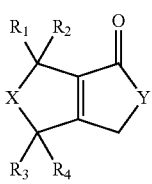

Structure II

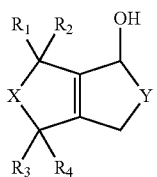

Structure III wherein, $R_1$, $R_2$, $R_3$ and $R_4$ stand for alkyl groups, X stands for —$CHR_5$— or —$CHR_5$—$CHR_6$—, Y stands for —$CHR_7$— or —$CHR_7$—$CHR_8$— and $R_5$, $R_6$, $R_7$ and $R_8$ stand for hydrogen or alkyl groups.

Examples of bicyclic compounds as raw material include, for instance unsaturated bicyclic compounds, in which in each one of the rings at least five or six carbon atoms are contained. In this conformation, the present invention is particularly useful for the preparation of ketones and alcohols from tetra-alkyl- or poly-alkyl-substituted compounds. Examples thereof may be 1,1,3,3-tetra-alkyl- and higher poly-alkyl-substituted 1,2,3,4,5,6-hexahydropentalene, 4,4,7,7-tetra-alkyl- and 1,1,3,3-tetra-alkyl and higher poly-alkyl-substituted 4,5,6,7-tetrahydroindane and 1,1,4,4-tetra-alkyl- and higher polyalkyl-substituted 1,2,3,4,5,6,7,8-octahydronaphthaline or combinations thereof, without this being limiting.

The alkyl groups herein considered contain preferably from one to three carbon atoms. The differently represented alkyl groups from $R_1$ to $R_8$ can be the same or different from one another. Preferably, the alkyl groups from $R_1$ to $R_4$ are the same alkyl groups and are methyl groups. The groups from $R_5$ to $R_8$ can be the same or different from one another. Preferably, the group $R_5$ is hydrogen or a methyl group and the groups $R_6$ to $R_8$ are hydrogen.

Oxygen-containing gas is typically used as oxygen source. This oxygen-containing gas may be, for example, air, pure oxygen, or air or pure oxygen diluted with inert gas, such as nitrogen, argon and helium. Oxygen enriched air in which pure oxygen is added to air can also be used.

With regard to the present invention, metal-organic compounds can be used as oxidation catalysts, which contain one or more metal atoms and between 4 to 30 carbon atoms. On the one hand, the catalyst can be a metal salt derived from an aliphatic carboxylic acid (e.g. acetate, propionate, etc.) or a metal salt derived from an aryl carboxylic acid (e.g. naphthenate), or combinations thereof. The catalyst can also be found in the form of a coordination complex (e.g. acetyl acetonate). On the other hand, the catalyst can contain metal atoms such as nickel, cobalt, copper, manganese, or combinations thereof. The catalyst can also contain halogen atoms (e.g. chlorine, bromine, etc.). The catalyst can be used in the pure form of its metal-organic compound or metal salt, or alternatively can be found in the form of a homogeneous solution, the vehicle for which may be or is a mixture of paraffinic compounds, namely mineral spirits. Preferably, selected catalysts are cobalt and copper acetate and cobalt-naphthenate.

The weight metal content in the metal-organic compound under any of the forms as described beforehand, is comprised between 0.001 and 35%, more preferably between 0.5 and 15%.

With regard to the present invention, gold can be supported on an inorganic or an organic support. Gold can be supported with the aim of increasing its dispersion, hence reducing the particle size onto the support. According to this, gold can be applied either in its metallic or its ionic form.

The weight metal content of gold with respect to the inorganic solid support, as specified later on, is comprised between 0.1 and 20% gold, more preferably between 0.5 and 10% gold.

The said support can be selected from among iron oxide, titanium oxide, cerium oxide, magnesium oxide, zirconium oxide, silica gel, silicic acid, lanthanum oxide, alumina, zinc oxide, calcium carbonate, calcium phosphate, calcium sulphate, barium sulphate, lead sulphate, lead oxide, lead carbonate, charcoal and combinations thereof. Preferably, the said support can be selected from iron oxide, titanium oxide, cerium oxide, zirconium oxide and combinations thereof. More preferably, the said support can be selected from titanium oxide, cerium oxide and combinations thereof.

Examples of a method for supporting gold on any of the aforementioned supports include, for example, a method such as to impregnate the support with an aqueous solution of gold compounds, such as halogen acid of gold and salts thereof, a method such as to immerse the support in an aqueous solution of gold compounds and adsorb gold compounds with the support and the like. Another preparation method involves the deposition of gold on the support (carrier) by precipitation forming an insoluble compound, as for instance an hydroxide. The supported gold catalyst can be calcined in air or in an inert atmosphere, and even reduced in $H_2$, or combinations of such treatments.

The oxidation reaction of bicyclic compounds can be performed in two stages. In the first stage, the oxidation reaction of bicyclic compounds can be performed by contacting the bicyclic compounds with an oxygen containing gas, such as oxygen, in the presence of a metal-organic compound. The quantity of a catalyst used is typically 0.01 to 20 parts by weight with respect to 100 parts by weight of bicyclic compounds, preferably 0.1 to 10 parts by weight. The molar relationship of bicyclic compound (substrate, hereafter) to metal contained in the catalyst can be considered between 1.5 and 150000.

In the second stage, the oxidation reaction of bicyclic compounds can be performed by contacting the bicyclic compounds resulting from the first stage, as specified beforehand, see previous paragraph, with or without any appropriate work-up treatment (e.g. cobalt precipitation), with an oxygen containing gas, such as oxygen, in the presence of a supported gold catalyst. The quantity of a catalyst used is typically 0.01 to 50 parts by weight with respect to 100 parts by weight of bicyclic compounds, preferably 0.1 to 40 parts by weight. The molar relationship of substrate to metal contained in the catalyst can be considered between 1.5 and 15000.

In the method of the present invention, a base can be used. The base can be selected from an inorganic base or an organic base or combinations thereof. Preferably, inorganic bases can be selected from alkaline and/or earth-alkaline hydroxides, carbonates or phosphates, or mixtures thereof, without being this limiting. More preferably, inorganic bases can be selected from LiOH, NaOH, KOH, Be(OH)$_2$, Mg(OH)$_2$, Ca(OH)$_2$, or mixtures thereof, without this being limiting. Preferably, organic bases can be selected from alkaline alcoholates, phosphazenes, amines, or quaternary ammonium hydroxide. More preferably, bases can be selected from sodium methoxide, ethoxide, n-butoxide, sec-butoxide, tert-butoxide, or mixtures thereof, without being this limiting. Nevertheless, combinations of the aforementioned bases are not discarded.

In the method of the present invention, water can be present, either as evolved concomitant water under the oxidation conditions or as deliberately added water from the beginning, in any of the stages mentioned before.

In the method of the present invention, a free-radical initiator can be used. The introduction of a free-radical initiator can be advantageous to improve the conversion of the bicyclic compound used as reactant. Examples of a free-radical initiator include azonitrile compounds such as 2,2'-azobis (isobutyronitrile), 2,2'-azobis(2,4-dimethylvaleronitrile) and 2,2'-azobis(4-methoxy-2,4-dimethylvaleronitrile), and peroxides such as peroxydibenzoyl, peroxydilauroyl, peroxyditert-butyl, tert-butylperoxy-2-ethylhexanoate and bis(2-ethylhexyl)peroxydicarbonate. Combinations of two or more radical initiators may be used together as required. Among them, azonitrile compounds, as for instance 2,2'-azobis (isobutyronitrile) are preferred. The quantity of a free-radical initiator is typically equal or inferior to 10 mol % with respect to the substrate.

The reaction temperature is typically between 25 and 200° C., preferably 80 to 160° C. The reaction pressure is typically 0.01 to 10 MPa, preferably 0.1 to 2 MPa.

In the method of the present invention, the use of solvents is optional. If a solvent is to be used, preferred solvents include nitriles such as acetonitrile and benzonitrile, halogen- or non-halogen-containing alkyl and/or aromatic solvents, such as, benzene, toluene and trifluorotoluene, carboxylic acid solvents, such as acetic acid and propionic acid, and combinations thereof. Other solvents that can be used are saturated, partially unsaturated and/or conjugated-double-bonded bicyclic compounds under a similar or derivatized configuration to the aforementioned reactant, which typically result from hydrogenating processes performed upstream of the process circumscribed to the method of the present invention. Although the role of solvents must be directed to the purposes as stated in the current state-of-the-art, the oxidation of said solvent up to a low degree of conversion is not discarded, regardless of the reaction conditions. The use of solvent is not restricted by the need for any base present to be soluble in the reaction medium under the reaction conditions whatsoever.

In the method of the present invention, the equilibrium can be shifted by removing from the reaction media some of the products, for instance, water.

The after-treatment after oxidation reaction is not particularly limited, for example including a process, such as to filter the reaction mixture to separate a catalyst therefrom, which mixture is thereafter washed with solvents (e.g. water, acetone) and subsequently distilled. In the case where a bicyclic-hydroperoxide corresponding to the reactant is contained in the reaction mixture, it can be converted into the intended allylic alcohol or ketone by decomposing the peroxides with methods well known in the art.

Further embodiments and features of the invention will now be described by means of the following numbered paragraphs:

1. A method for the allylic oxidation, characterized in that bicyclic compound reactants with the following general Structure I:

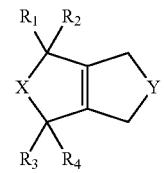

wherein $R_1$, $R_2$, $R_3$ and $R_4$ stand for alkyl groups, X stands for —$CHR_5$— or —$CHR_5$—$CHR_6$—, Y stands for —$CHR_7$— or —$CHR_7$—$CHR_8$— and $R_5$, $R_6$, $R_7$ and $R_8$ stand for hydrogen or alkyl groups, are oxidized with an oxygen-containing gas in presence of metal-organic compounds and a supported gold catalysts, in order to obtain α,β-unsaturated ketones and/or alcohols, wherein a carbonyl and/or a carbinol group is in the Y-containing ring.

2. A method according to paragraph 1, characterized in that the oxygen-containing gas can be selected from oxygen, air, stripped air, enriched air or mixtures thereof, being the remaining any inert gas.

3. A method according to paragraph 1, characterized in that the metal-organic compounds used as catalysts can contain one or more metal atoms and between 4 and 30 carbon atoms.

4. A method according to paragraph 3, characterized in that the metal-organic compounds used as catalysts can be a metal salt derived from an aliphatic, an aryl carboxylic acid, or combinations thereof, or a coordination complex, or mixtures thereof.

5. A method according to paragraph 3, characterized in that the metal-organic compounds used as catalysts can contain metal atoms from among nickel, cobalt, copper, manganese, or combinations thereof.

6. A method according to paragraph 3, characterized in that the metal-organic compounds used as catalysts can be used in its pure form or in the form of a homogeneous solution being the solvent a mixture of paraffinic compounds.

7. A method according to paragraph 3, characterized in that the metal-organic compounds used as catalysts have a metal content comprised between 0.001 and 35 weight %.

8. A method according to paragraph 7, characterized in that the metal-organic compounds used as catalysts have a metal content comprised between 0.5 and 15 weight %.

9. A method according to anyone of paragraphs 1, 3, 4, 5, 6, 7 and 8, characterized in that the molar relationship of reactant to metal contained in the catalyst can be considered between 1.5 and 15000.

10. A method according to paragraph 1, characterized in that the gold is supported on an inorganic or organic support, which can be selected from among iron oxide, titanium oxide, cerium oxide, magnesium oxide, zirconium oxide, silica gel, silicic acid, lanthanum oxide, alumina, zinc oxide, calcium carbonate, calcium phosphate, calcium sulphate, barium sulphate, lead sulphate, lead oxide, charcoal and combinations thereof.

11. A method according to paragraph 10, characterized in that the gold can be supported on cerium oxide.

12. A method according to paragraph 10, characterized in that weight metal content of gold with respect to the support can be comprised between 0.1 and 20% gold.

13. A method according to paragraph 12, characterized in that weight metal content of gold with respect to the support can be comprised between 0.5 and 10% gold.

14. A method according to anyone of paragraphs 10, 11, 12, and 13, characterized in that the molar relationship of reactant to gold contained in the catalyst can be considered between 1.5 and 15000.

15. A method according to paragraph 1, characterized in that an organic, inorganic base or mixtures thereof can be introduced in the reaction system.

16. A method according to paragraph 1, characterized in that a free-radical initiator can be used.

17. A method according to paragraph 6, characterized in that the free-radical initiator can be selected from azonitrile compounds and peroxides, or combinations thereof.

18. A method according to paragraph 1, characterized in that the process can be performed at a temperature between 0° C. and 200° C., and at a pressure between 0.01 and 10 MPa.

19. A method according to paragraph 18, characterized in that the process can be performed at a temperature between 40° C. and 180° C., and at a pressure between 0.1 and 2 MPa.

20. A method according to paragraph 1, characterized in that a solvent can be used.

21. A method according to paragraph 20, characterized in that the solvent can be a nitrile solvent, a halogen- or non-halogen-containing alkyl and/or aromatic solvent, a carboxylic acid solvent, and combinations thereof.

22. A method according to paragraph 20, characterized in that the solvent can be a saturated, partially unsaturated and/or conjugated-double-bonded bicyclic compound under a similar or derivatized configuration to the reactant, and combinations thereof.

23. A method according to paragraph 1, characterized in that the said allylic oxidation can be performed in two consecutive stages.

24. A method according to anyone of paragraphs 1, 2, 3, 4, 5, 6, 7, 8, 9 and 23, characterized in that the first stage is carried out by contacting the bycyclic compound with an oxygen-containing gas and in presence of metal-organic compounds as catalysts.

25. A method according to anyone of paragraphs 1, 10, 11, 12, 13, 14, 15, 16, 17, 18, 20, 21, 22, 23 and 24, characterized in that the reaction mixture resulting from the first stage is used in a second stage, wherein the gold catalyst is added.

26. A method according to anyone of paragraphs 24 and 25, characterized in that the reaction mixture resulting from the first stage can be treated prior to its use in the second stage in order to remove any of the formed products, unreacted bicyclic compounds, solvents, or catalyst.

EXAMPLES

The following examples are selected with the aim of illustrating the methods of preparation of catalysts and the performance of reactions described beforehand, using the already described materials, and, unless stated otherwise, without intending to impose limitations on reaction conditions, possible candidate active materials thereof, etc.

Example 1

Preparation of Gold Nanoparticles Supported on Nanoparticulated Ceria (Au—$CeO_2$)

For the preparation of nanoparticulated ceria, an aqueous solution of $Ce(NO_3)_4$ (375 mL, 0.8 M) was treated, under stirring and at ambient temperature, with an aqueous solution of ammonia (1.12 L, 0.8 M). The dispersion of $CeO_2$ nanoparticles (particle diameter less than or equal to 10 nm) was heated in a PET vessel at 100° C. for 24 h. The resulting yellow precipitate was filtered and dried under vacuum overnight. The cerium oxide synthesized has, owing to the small size of the nanoparticles, a high surface area (180 $m^2$/g).

Gold was deposited on the nanoparticulated ceria by using the following procedure: a solution of $HAuCl_4.3H_2O$ (350 mg) in deionised water (160 mL) was brought to pH 10 by addition of a solution of NaOH 0.2 M. Once the pH value was stable the solution was added to a gel containing colloidal $CeO_2$ (4.01 g) in $H_2O$ (50 mL). After adjusting the pH of the slurry at a value of 10 by addition of a 0.2 M solution of NaOH 0.2 M, the slurry was continuously stirred vigorously for 18 h at RT. The Au—$CeO_2$ solid was then filtered and exhaustively washed with several litres of distilled water until no traces of chlorides were detected by the $AgNO_3$ test. The catalyst was dried under vacuum at room temperature for 1 h. The total Au content of the final catalyst was 2.6 wt % as determined by chemical analysis.

Example 2

In a three-necked-round flask, 37 mg cobalt-naphthenate catalyst (ALDRICH, 6 wt % Co in mineral spirits) (Co-Naph, hereafter) were added to 14 g of an olefin/paraffin mixture containing 60 weight % 4,5,6,7-tetrahydro-1,1,2,3,3-pentamethylindane (THPMI hereafter), being the remaining fully saturated or aromatic derivatives from the previous compound, and 350 mg distilled water. The contents were heated up to 125° C. and magnetically stirred at 1000 rpm. When the desired temperature was reached (after c.a. 30 sec), air was fed at 0.66 mL/s. The progress of the reaction was followed by taking samples at regular periods and analyzed by GC/MS. N-hexadecane was used as the external standard. Peroxides were determined by adding a triphenylphosphine solution in acetone to the reaction sample. After 17 hours of reaction c.a. 56 mol % THPMI conversion was obtained, 26 mol % 1,2,3, 5,6,7-hexahydro-1,1,2,3,3-pentamethyl-4H-inden-4-one and 21 mol % 4,5,6,7-tetrahydro-1,1,2,3,3-pentamethyl-4-indanol. This part comprises the first stage of the process in accordance with the earlier description of the invention. In the second stage of the process, 3 g of the above resulting mixture was directly taken, without further after-treatment, and 100 mg Au—$CeO_2$ catalyst, prepared according to Example 1, were added. The contents were heated up to 125° C. and magnetically stirred at 1000 rpm. When the desired temperature was reached (after c.a. 30 sec), air was fed at 0.66 mL/s. The progress of the reaction was followed by taking samples at regular periods and analyzed by GC/MS. N-hexadecane was used as the external standard. Once again, peroxides were determined by adding a triphenylphosphine solution in acetone to the reaction sample. After 24 hours of reaction and the yield of 1,2,3,5,6,7-hexahydro-1,1,2,3,3-pentamethyl-4H-inden-4-one was 47 mol % with less than 1 mol % yield to 4,5,6,7-tetrahydro-1,1,2,3,3-pentamethyl-4-indanol, being the remaining polyoxygenated by-products.

Example 3

In a three-necked-round flask, 100 mg Au—$CeO_2$ catalyst, prepared according to Example 1, were added to 3 g THPMI (as in Example 2). The contents were heated up to 125° C. and magnetically stirred at 1000 rpm. When the desired temperature was reached (after c.a. 30 sec), air was fed at 0.66 mL/s. The progress of the reaction was followed by taking samples at regular periods and analyzed by GC/MS. N-hexadecane was used as the external standard. Peroxides were determined by adding a triphenylphosphine solution in acetone to the reaction sample. After 48 hours of reaction c.a. 19 mol % THPMI conversion was obtained, 17 mol % 1,2,3,5,6,7-hexahydro-1,1,2,3,3-pentamethyl-4H-inden-4-one and 1 mol % 4,5,6,7-tetrahydro-1,1,2,3,3-pentamethyl-4-indanol.

It will be appreciated that many optional features of embodiments of the invention can be used in any combination (and in any number) with other features. This includes, but is not limited to combining the features of any of the dependent claims with the independent claims, in any number and in any combination. All of the dependent claims could be considered, for the purposes of disclosure of possible variants, to be dependent from any preceding claim.

The invention claimed is:

1. A method of allylic oxidation, characterized in that a bicyclic compound reactant with the following general Structure I:

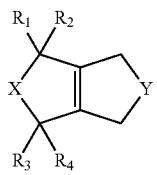

wherein $R_1$, $R_2$, $R_3$ and $R_4$ stand for alkyl groups, X stands for —$CHR_5$— or —$CHR_5$—$CHR_6$—, Y stands for —$CHR_7$— or —$CHR_7$—$CHR_8$— and $R_5$, $R_6$, $R_7$ and $R_8$ stand for hydrogen or alkyl groups, is oxidized with an oxygen-containing gas in presence of a metal-organic compound and a supported gold catalyst, in order to obtain an α,β-unsaturated ketones and/or alcohols, wherein a carbonyl and/or a carbinol group is in the Y-containing ring.

2. A method according to claim 1, characterized in that the oxygen-containing gas is selected from oxygen, air, stripped air, enriched air, mixtures thereof, or mixtures of any one or more of the aforementioned gases with an inert gas.

3. A method according to claim 1, characterized in that the metal-organic compound comprises one or more metal atoms and between 4 and 30 carbon atoms.

4. A method according to claim 3, characterized in that the metal-organic compound is a metal salt derived from an aliphatic carboxylic acid, an aryl carboxylic acid, or combinations thereof, or a coordination complex, or mixtures thereof.

5. A method according to claim 3, characterized in that the metal-organic compound comprises metal atoms from among nickel, cobalt, copper, manganese, or combinations thereof.

6. A method according to any one of claim 3, characterized in that the metal-organic compound is used in its pure form or in the form of a homogeneous solution the solvent being a mixture of paraffinic compounds.

7. A method according to any one of claim 3, characterized in that the metal-organic compound have a metal content comprised between 0.001 and 35 weight %.

8. A method according to claim 7, characterized in that the metal-organic compound have a metal content comprised between 0.5 and 15 weight %.

9. A method according to claim 1, characterized in that the molar relationship of reactant to metal contained in the metal-organic compound is considered between 1.5 and 15000.

10. A method according to claim 1, characterized in that the gold is supported on an inorganic or organic support, which is selected from among iron oxide, titanium oxide, cerium oxide, magnesium oxide, zirconium oxide, silica gel, silicic acid, lanthanum oxide, alumina, zinc oxide, calcium carbonate, calcium phosphate, calcium sulphate, barium sulphate, lead sulphate, lead oxide, charcoal and combinations thereof.

11. A method according to claim 10, characterized in that the gold is supported on cerium oxide.

12. A method according to claim 10, characterized in that weight metal content of gold with respect to the support is between 0.1 and 20 weight % gold.

13. A method according to claim 10, characterized in that weight metal content of gold with respect to the support is between 0.5 and 10 weight % gold.

14. A method according to claim 1 characterized in that the molar relationship of reactant to gold contained in the catalyst is between 1.5 and 15000.

15. A method according to claim 1, characterized in that an organic, inorganic base or mixtures thereof is introduced in the reaction system.

16. A method according to claim 1, characterized in that a free-radical initiator may optionally be used.

17. A method according to claim 16, characterized in that the free-radical initiator is selected from azonitrile compounds and peroxides, or combinations thereof.

18. A method according to claim 1, characterized in that the process is performed at a temperature between 0° C. and 200° C., and at a pressure between 0.01 and 10 MPa.

19. A method according to claim 18, characterized in that the process is performed at a temperature between 40° C. and 180° C., and at a pressure between 0.1 and 2 MPa.

20. A method according to claim 1, characterized in that a solvent may optionally used.

21. A method according to claim 20, characterized in that the solvent is selected from a nitrile solvent, a halogen- or non-halogen-containing alkyl and/or aromatic solvent, a carboxylic acid solvent, and combinations thereof.

22. A method according to claim 20, characterized in that the solvent is a saturated, partially unsaturated and/or conjugated-double-bonded bicyclic compound under a similar or derivatized configuration to the reactant, and combinations thereof.

23. A method according to claim 1, characterized in that the said allylic oxidation is performed in two consecutive stages.

24. A method according to claim 23, characterized in that the first stage is carried out by contacting the bicyclic compound with an oxygen-containing gas and in presence of metal-organic compounds as catalysts.

25. A method according to claim 23, characterized in that the reaction mixture resulting from the first stage is used in a second stage, wherein the gold catalyst is added.

26. A method according to anyone of claim 23, characterized in that the reaction mixture resulting from the first stage is treated prior to its use in the second stage in order to remove any of the formed products, unreacted bicyclic compounds, solvents, or catalyst.

* * * * *